US008679806B2

(12) United States Patent  
Levon et al.

(10) Patent No.: US 8,679,806 B2
(45) Date of Patent: Mar. 25, 2014

(54) METHODS FOR DETECTING AND/OR QUANTIFYING A CONCENTRATION OF SPECIFIC BACTERIAL MOLECULES USING BACTERIAL BIOSENSORS

(75) Inventors: Kalle Levon, Brooklyn, NY (US); Bin Yu, West Hartford, CT (US); Yanxiu Zhou, West Hartford, CT (US)

(73) Assignee: Polytechnic Institute of New York University, Brooklyn, NY (US)

( * ) Notice: Subject to any disclaimer, the term of this patent is extended or adjusted under 35 U.S.C. 154(b) by 566 days.

(21) Appl. No.: 12/176,942

(22) Filed: Jul. 21, 2008

(65) Prior Publication Data

US 2009/0061464 A1 Mar. 5, 2009

Related U.S. Application Data

(63) Continuation of application No. 10/888,530, filed on Jul. 9, 2004, now abandoned.

(60) Provisional application No. 60/486,088, filed on Jul. 10, 2003.

(51) Int. Cl.
*C12N 13/00* (2006.01)
*C12N 11/00* (2006.01)
*G01N 33/53* (2006.01)
*C12Q 1/00* (2006.01)

(52) U.S. Cl.
USPC ............ 435/173.1; 435/4; 435/6.15; 435/7.1; 435/40.5; 435/41; 435/174; 435/176; 435/177; 435/180; 435/285.2; 435/287.1

(58) Field of Classification Search
None
See application file for complete search history.

(56) References Cited

U.S. PATENT DOCUMENTS

| | | | |
|---|---|---|---|
| 5,622,872 A * | 4/1997 | Ribi | 436/518 |
| 6,329,209 B1 * | 12/2001 | Wagner et al. | 506/13 |
| 6,387,614 B1 * | 5/2002 | Cheng et al. | 435/4 |
| 2001/0026915 A1 * | 10/2001 | Charych et al. | 435/5 |

OTHER PUBLICATIONS

Bilewicz et al., 1991. Langmuir. vol. 7:2794-2802.*
Feignier et al, (FEMS Microbio. Letters. 1995. vol. 127:11-15).*
Paddle (Biosensors & Bioelectronics. 1996. vol. 11(11 ): 1079-1113).*

* cited by examiner

*Primary Examiner* — Ja'na Hines
(74) *Attorney, Agent, or Firm* — Frommer Lawrence & Haug LLP; Stephen J. Lieb (57) ABSTRACT

A real-time method employing a portable peptide-containing potentiometric biosensor, can directly detect and/or quantify bacterial spores. Two peptides for specific recognition of *B. subtilis* and *B. anthracis* Sterne may be immobilized by a polysiloxane monolayer immobilization (PMI) technique. The sensors translate the biological recognition event into a potential change by detecting, for example, *B. subtilis* spores in a concentration range of 0.08-7.3×10$^4$ CFU/ml. The sensing method exhibited highly selective recognition properties towards *Bacillus subtilis* spores over other kinds of spores. The selectivity coefficients of the sensors for other kinds of spores are in the range of 0-1.0×10$^{-5}$. The biosensor method not only has the specificity to distinguish *Bacillus subtilis* spores in a mixture of *B. subtilis* and *B. thuringiensis* (*thur.*) Kurstaki spores, but also can discriminate between live and dead *B. subtilis* spores. Furthermore, the sensing method can distinguish a *Bacillus subtilis* 1A700 from other *B. subtilis* strain. Assay time may be as low as about 5 minutes for a single test. Rapid identification of *B. anthracis* Sterne and *B. anthracis* ΔAmes was also provided.

18 Claims, 12 Drawing Sheets

Sensor could capture 98% *B. subtilis*

METHODS FOR DETECTING AND/OR QUANTIFYING A CONCENTRATION OF SPECIFIC BACTERIAL MOLECULES USING BACTERIAL BIOSENSORS

§0 CROSS REFERENCE TO RELATED APPLICATIONS

This application is a continuation of U.S. patent application Ser. No. 10/888,530 (incorporated herein by reference) titled "BACTERIAL BIOSENSORS," filed on Jul. 9, 2004 now abandonded and listing Kalle LEVON, Bin Y U and Yanxiu ZHOU as inventors, which claims the benefit of U.S. Provisional Patent Application Ser. No. 60/486,088 (incorporated herein by reference), titled "BACTERIAL BIOSENSOR," filed on Jul. 10, 2003 and listing Kalle Levon, Bin Yu, and Yanxiu Zhou as inventors.

§1. BACKGROUND

§1.1 Field of the Invention

This invention relates generally to the field of sensors and in particular to biosensors specific to biological/chemical agents and bacterium such as *Bacillus anthracis*.

§1.2 Background of the Invention

The potential use of anthrax, and in particular the spores of *Bacillus anthracis* (BA) as a weapon of biological terrorism has rekindled interest in devices and methods for the rapid detection and identification of biological or chemical agents. Such interest has become particularly acute since the September 11 attacks and the anthrax-by-mail terrorism.

Devices and methods for detecting biological or chemical agents should be rapid, specific, easy to use and transport, and very sensitive since a single pathogenic organism may be an infectious dose in some cases. Consequently, it is important to assess and begin treatment early for individuals exposed to such organisms. Additionally, it is equally important to know whether a person exhibiting general symptoms is suffering from, for example, anthrax exposure, or a less serious ailment for which totally different (or perhaps antagonistic) treatments are indicated.

§1.3 Related Art

Significant technological progress has been made in the detection and analysis of biological and chemical agents over the past decade. (See, for example: Ivnitski, D., Abdel-Hamid, I., Atanasov, P., Wilkins, E. *Biosensors Bioelectron.*, 1999, 14, 599-624 and references therein (875); and Iqbal, S. S., Mayo, M. W., Bruno, J. G., Bronk, B. V., Batt, C. A., Chambers, J. P. *Biosensor Bioelectron.*, 2000, 15, 549-578 and references therein (881).)

The outer face of macromolecular biological assemblies like viruses or bacteria includes a proteinaceous capsid, a membrane composed of glycoproteins and lipids, or a cell wall. Accordingly, they carry charged or chargeable groups on their outer surface creating an electric double layer upon contact with the aqueous phase. (See, for example: Kenndler, E., Blass, D. *Trends in Anal. Chem.*, 2001, 20(10), 543-551; and Lanza, R. P., Langer, R., Chick, W. L. (Eds). When a biological recognition component for bacterial spores, such as a peptides, nucleic acids (See, for example, Park, S.-J, Taton, T. A., Mirkin, C. A. *Science*, 2002, 295, 1a503-1506.), apatamers (See, for example, Bruno, J. G., Kiel, J. L. *Biosensor Bioelectron.*, 1999, 14, 457-464.), or antibodies (See, for example, Zhou, B., Wirsching, P., Janda, K. D. *PNAS*, 2002, 99, 5241-5246.) are incorporated in/on a sensing layer of an electrode, the bacterial spores can be recognized by a biospecific reaction which takes place between the biological recognition component and bacterial spores—without any preconcentration or separation process.

In particular embodiments, bacterial spores (receptor) and peptide, which is fixed on the surface of substrate, associate in solution to form a peptide-spores biological complex. The residual potential due to complementarity between the peptide (the complementary ligand) and the bacterial spores (receptor) with the best possible electrostatic free energy change, is equal in magnitude and opposite in sign to the ligand desolvation potential everywhere within the ligand including on the ligand surface. (See, for example: Honig, B., Nicholls, A. *Science*, 1995, 268, 1144-1149; Honig, B., Sharp, K., Yang, A.-S. *J. Phys. Chem.*, 1993, 97, 1101-1109; Lee, L.-P., B. Tidor, B. *J. Chem. Phys.*, 1997, 106, 8681-8690; Chong, L. T., Dempster, S. E., Hendsch, Z. S., Lee, L-P., Tidor, B. *Protein Sc.*, 1998, 7, 206-210; and Kangas, E., Tidor, B. *J. Chem. Phys.*, 1998, 109, 7522-7545.) Under the electromotive force (potentiometry), the surface electrostatic potentials of the peptide-spores complex formed relates to the specific biorecognition process enabling bacterial spores to be identified and detected by potentiometry.

Many of the technologies developed and/or currently being used however, such as FT-IR spectroscopy, fluorescence spectroscopy, polymerase chain reaction ("PCR"), flow cytometry, impedimetry, UV resonant Raman spectroscopy, and others, are large, expensive, or require sophisticated, relatively time-consuming, and often extensive analysis procedures.

Accordingly, devices and methods which facilitate the accurate, quick, convenient and inexpensive detection of biological or other chemical agents are of significant scientific and societal interest.

In view of the limitations in the art, a flexible method for selectively detecting a wide range of molecules is needed. Additionally, it is desirable that such methods and devices constructed therefrom be applicable to the detection of biological or other chemical agents.

Such methods and devices are the subject of the instant invention.

§2. SUMMARY OF THE INVENTION

We have developed methods for using biosensors for the sensing/detection of biological or chemical agents of significant interest. Our inventive methods and sensors may involve biological and/or chemical recognition components (selectors or probes) immobilized on a substrate by using a polymer layer, such as a Polysiloxane Monolayer immobilization (PMI). The PMI method may be used to immobilize the selectors on the substrate by forming a physical bond between the monolayer and the selector (e.g., by adsorption).

In one embodiment, a monolayer of polysiloxane is polymerized on a substrate, onto which selector molecules are adsorbed. The resulting immobilized selector molecules is then used to interact with specific molecules (targets) within a mixture of molecules. Those specific molecules are detected and/or quantified via potentiometry.

§3. BRIEF DESCRIPTION OF THE DRAWINGS

Further features and aspects of the present invention may be readily understood from the Drawing in which:

FIGS. 7(A) and 7(B) are graphs showing the influence of peptide concentration in the ODS-CHCl$_3$/CCl$_4$ deposition solution and the effect of the co-adsorption time on the potentiometric response of peptide/ODS IT 
nition elements. Additionally, selectors may be hydrophobic or hydrophilic, cationic or anionic, and may be biologically active. Furthermore, other elements and/or structures may exist between the selector molecule(s) and substrate. (See, e.g., U.S. Provisional Application Serial No. 06/370,502 (incorporated herein by reference), titled "DENDRIMER SENSOR FOR *BAELILLUS SUBTILIS* SPORES," filed on Apr. 5, 2002.

§4.2 Experimental Procedures for Sensor Development and Evaluation

EXPERIMENTAL

Chemicals and Biochemicals

Chloroform and carbon tetrachloride were distilled over $CaH_2$. Other chemicals were used without further purification. Peptides were purchased from Advanced ChemTech, Inc (Louisville, Ky.). Alexa Fluor™ 488 was obtained from Molecular Probe (Eugene, Oreg.). All aqueous solution was prepared from water purified using a Millipore System (Resistivity: 18.2 MΩcm) and sterilized by autoclaving.

Bacterial Spores

*Bacillus subtilis* 1A700 (*B. subtilis*), *B. thuringiensis* Kurstaki (*B. thur.* Kurstaki), *B. thuringiensis* B8 (*B. thur.* B8), *B. licheniformis*, *B. globigii*, *B. anthracis* Sterne, *B. anthracis* ΔAmes, *B. cereus* T, and *B. megaterium* ATCC 14581 were grown in our laboratories. *B. subtilis* ATCC 6633 was purchased from Raven Biological Laboratories (Omaha, Me.).

Indium Tin Oxide (ITO) Electrodes and Surface Modification

ITO-coated glass (CG-50IN-CUV), which had a surface resistance of 10 $\Omega/cm^2$ was purchased from Delta Technologies (Stillwater, Minn.). The substrates were cleaned with concentrated nitric acid, 0.02 M sodium hydroxide, and water, respectively. Before the modification, the substrates were dried under a stream of nitrogen. They were subsequently (effective surface area about $1\times4$ $cm^2$) immersed into a solution of 2:3 (v/v) $CHCl_3/CCl_4$ suspension containing octadecyltrichlorosilane (ODS) ($8\times10^{-4}$ M) and peptide (0.30 mg/ml) at 0° C. for four minutes. The electrode was allowed to stand overnight at −20° C. Then peptide sensors were washed with water to remove the un-immobilized peptide from the surface and ready for use. ODS modified electrode without the peptide was also prepared as a control.

Microscope Imaging

All microscope experiments were performed on a fluorescence Microscope, Nikon Eclipse E600 (Diagnostic Instruments, Inc). $7.2\times10^5$ CFU/ml *B. subtilis* spores were labeled with Alexa Fluor™ 488, and then mixed with the same amount of unlabeled *B. thur*. Kurstaki spores. A 1 μL mixture of the above spores was added to the surface of peptide/ODS sensors (or the control), and checked under both phase-contrast and fluorescence microscope. They were checked under the microscope again after incubating 10 minutes and washing thoroughly using sterile water to remove non-captured spores.

Electrochemical Measurement

Potentiometric experiments were performed with an Orion 920A Potentiometer. All measurements were made in 50 ml of pH 7.4 PBS buffer thermostated to 37° C., in a 100 mL working volume single-compartment electrochemical cell (EG&G), equipped with magnetic stirrer. The two-electrode system included an Ag/AgCl (saturated KCl) reference electrode and the peptide/ODS/ITO sensor (or the control) working electrode. Thereafter, the potential response of the sensor was defined as the difference between the electrode potential with and without bacterial spores in solution, i.e., $\Delta E=E_1-E_0$, where $E_0$ and $E_1$ are the electrode potentials before and after the addition of bacterial spores, respectively.

§4.3 Sensors for *B. subtilis* Spores and *B. antracis* Sterne

As can now be readily appreciated, our inventive PMI methods of immobilizing a selector molecule on a support surface have significant implications for sensor development. More specifically, PMI may be used to immobilize a selector on the surface of an electrode, creating a sensor that selectively recognizes a molecule that interacts with the selector. We have applied our invention to the fabrication of novel sensors for selectively detecting bacteria, amino acids, and target DNA.

In an exemplary embodiment of our inventive PMI methods, a PMI-modified sensor was developed for recognizing *Bacillus subtilis* spores and *Bacillus Antracis*. Advantageously, and unlike indirect sensors which are responsive to products of degraded spores (such as those produced by molecular imprinted polymers, e.g., dipicolinic acid), our inventive PMI-modified sensors are direct sensors in that they are responsive to intact spores.

To fabricate a bacterial sensor, and in particular the *B. subtilis* spores sensor, an ITO glass electrode may be used as the substrate and Peptide may be used as selectors. Treating the ITO glass electrode with NaOH replaces surface OH groups with ONa groups. The ITO glass electrode may then be coated by soaking it in a suspension of peptide selector molecules (~0.35 mg/ml) and $CHCl_3/CCl_4$ (a volume ratio of 2:3) containing 0.8 mM ODS for approximately four minutes. The selector/polymer-coated electrode is then dried overnight and then washed with water.

With further reference to FIG. 1, and as shown therein, the peptide 135 is immobilized between carbon chains on the ODS monolayer 137 using this fabrication method. Note further that the template was not washed out with water since the hydrophobic layer prevents water from approaching the template. A low polarity medium such as chloroform, however, may remove the template from the monolayer.

FIG. 2 shows an experimental assembly 200 of *B. subtilis* spore detection using potentiometry and a PMI-modified sensor. The detection assembly 200 includes a reference electrode 210 and the *B. subtilis* spore sensor 220, both attached to a potentiometer 230. In this configuration, the reference electrode 210 and sensor 220 are suspended in a solution 240 containing *B. subtilis* spores stirred by a magnetic stirrer 250. With this detection assembly 200, the specific interaction between immobilized peptide on the surface of the sensor 220 and *B. subtilis* spore, produces an electrochemical event which may be measured by potentiometry. To test the specificity of our inventive peptide/ODS sensor to *B. subtilis* spores, its detection, versus that of a control (e.g., a blank sensor) detection, of *B. subtilis* and *B. thur*. kurstaki spores was measured. FIG. 3A shows the sensitivity of the *B. subtilis* peptide/ODS sensor, and the insensitivity of the blank sensor, to *B. subtilis* spores. Advantageously, and as expected, neither sensor was sensitive to *B. thur*. kursaki spores, as shown in FIG. 3B. Similarly, FIG. 4 shows the insensitivity of the *B. subtilis* peptide/ODS sensor to various bacteria spores other than *B. subtilis* spores. These results demonstrate the high selectivity of the PMI-modified sensor to its target molecule.

Of further advantage, our inventive peptide/ODS sensor is sensitive to even a particular strain of *B. subtilis* spores. Turning our attention now to FIG. 5, it can be seen that our inventive sensor only identified the strain of bacteria (1A700) for which its immobilized peptides were specific. A different strain (ATCC 6633) went largely undetected by the sensor.

To further evaluate our inventive method and sensors, two heptapeptide ligands that bind species-specifically to spores of selected *Bacillus subtilis* and *anthracis* Sterne species were identified by Phase Display (Ph.D.) Ligand Screening System. These peptides were immobilized on the surface of ITO glass by Polysiloxane Monolayer Immobilization (PMI) in a manner as previously described.

Figure 1:
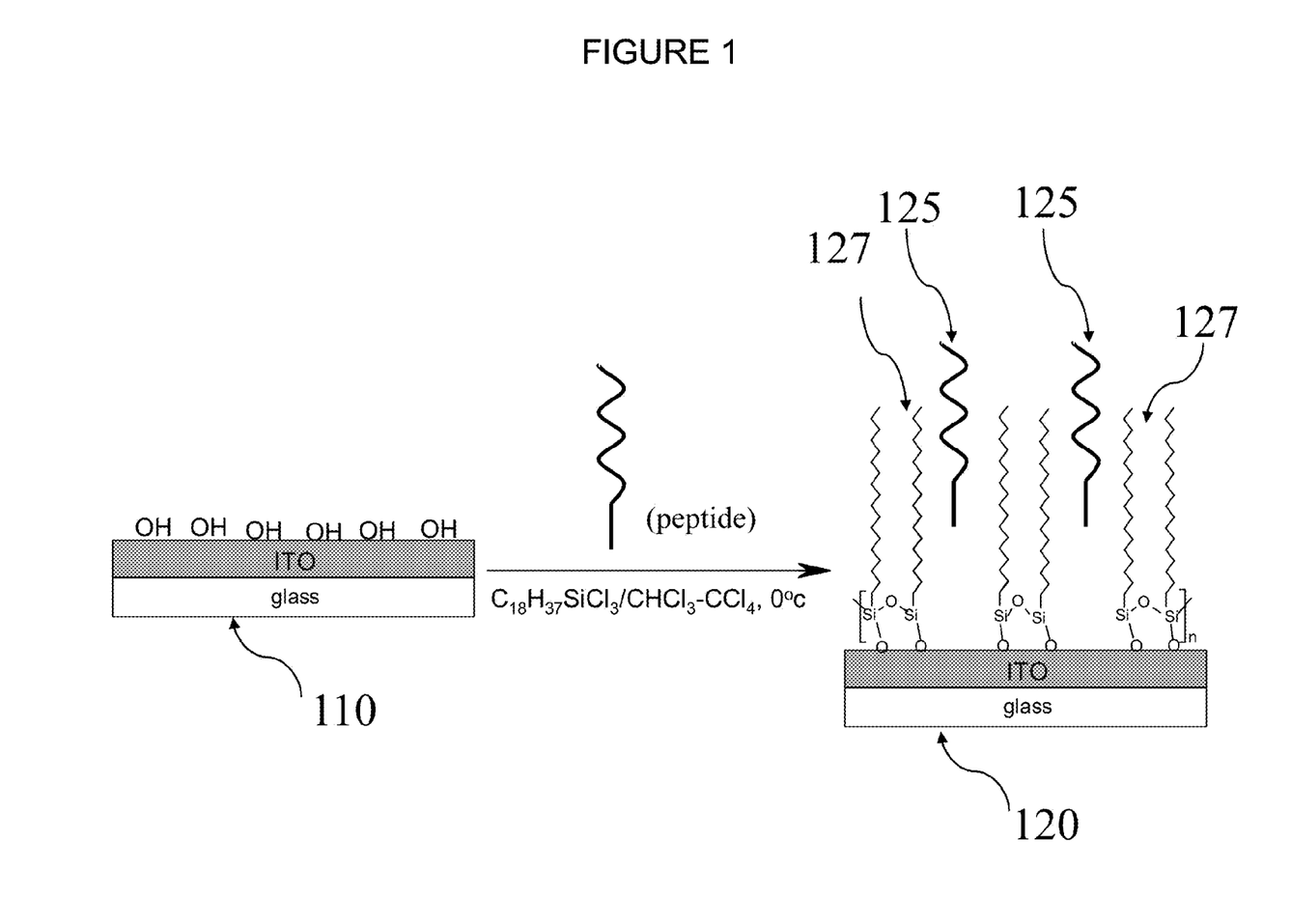
FIG. 1 is a diagram depicting PMI fabrication of a peptide/ODS sensor for bacterial spores.
Figure 2:
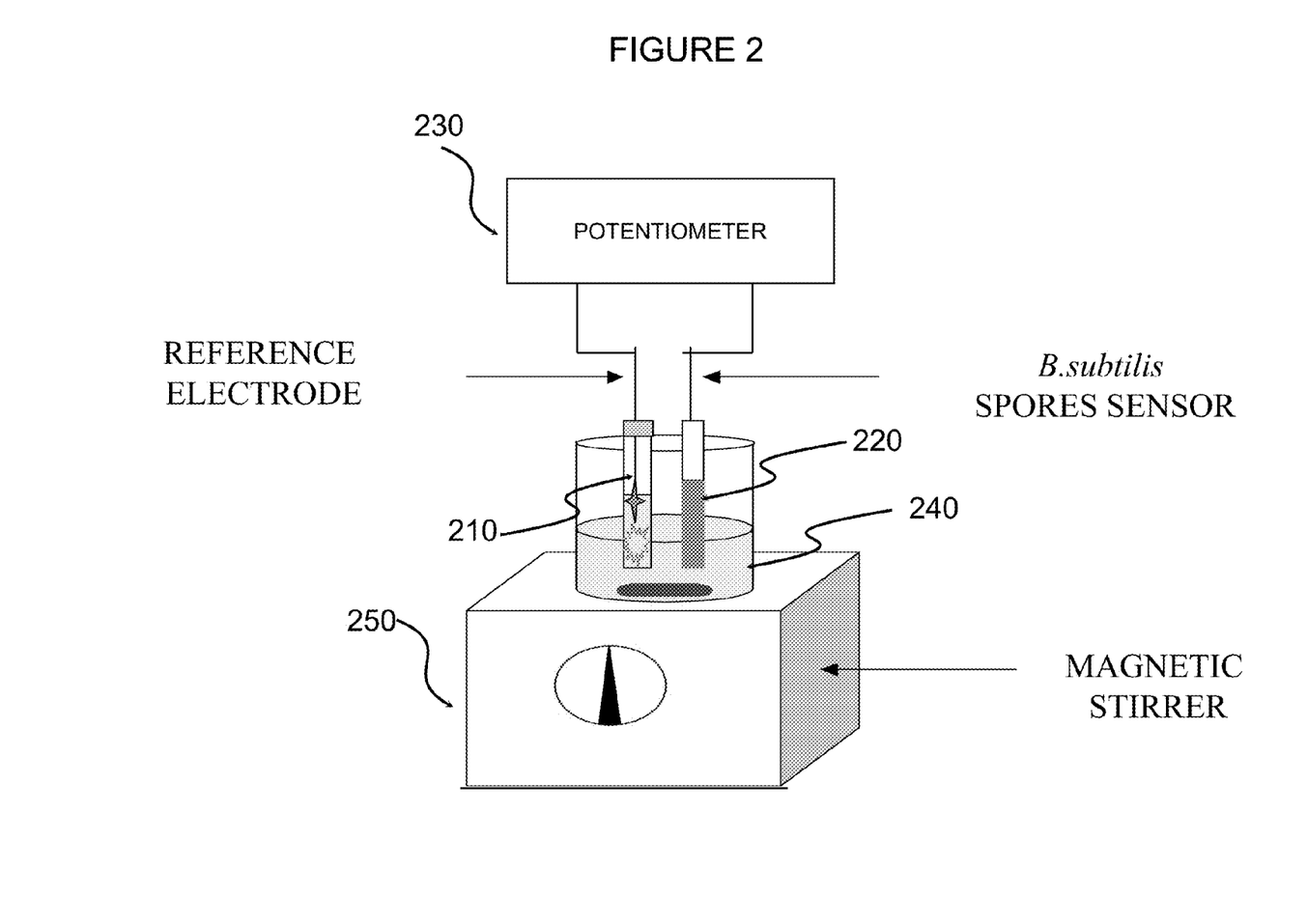
FIG. 2 is a diagram depicting the experimental assembly for detecting *B. subtilis* spores using potentiometry and a peptide/ODS sensor.
Figure 3A:
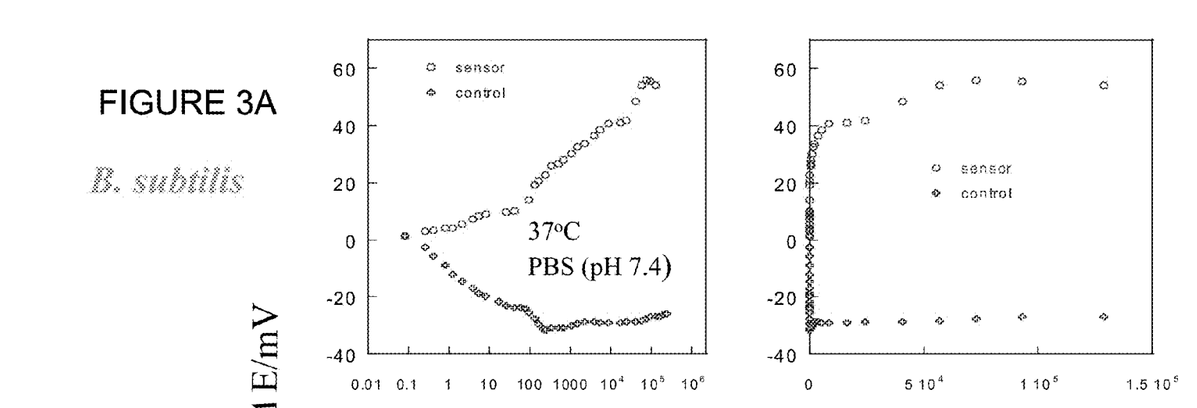
FIGS. 3a and 3b are graphs showing the potentiometric response of peptide/ODS sensor to *B. subtilis* and *Bacillus thurigiensis kursaki* spores, respectively.
Figure 3B:
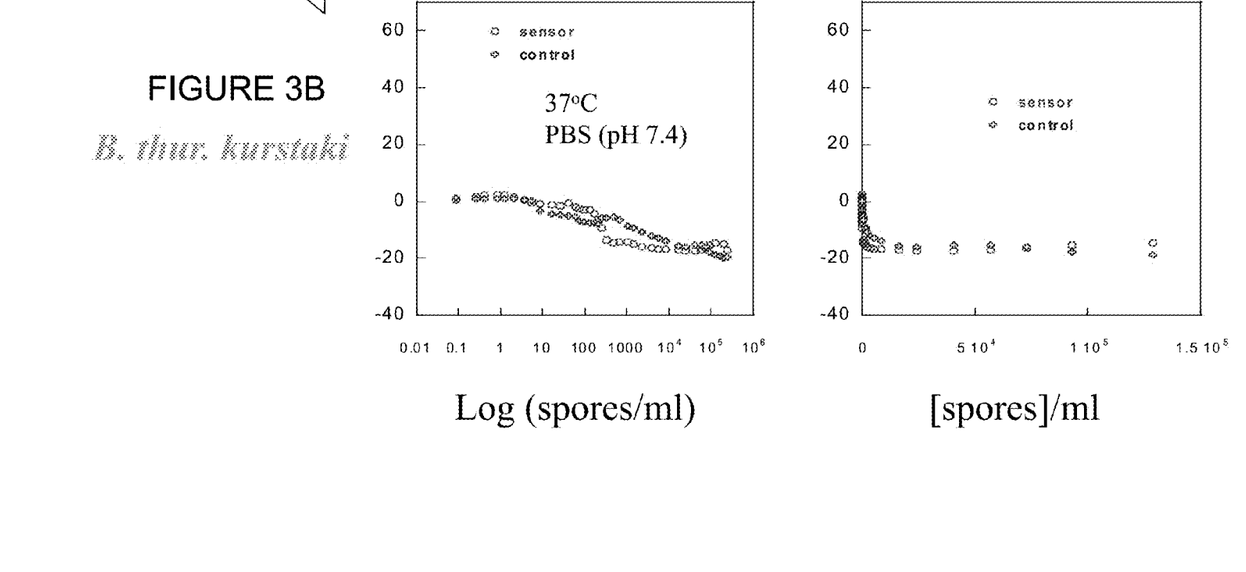
Figure 4:
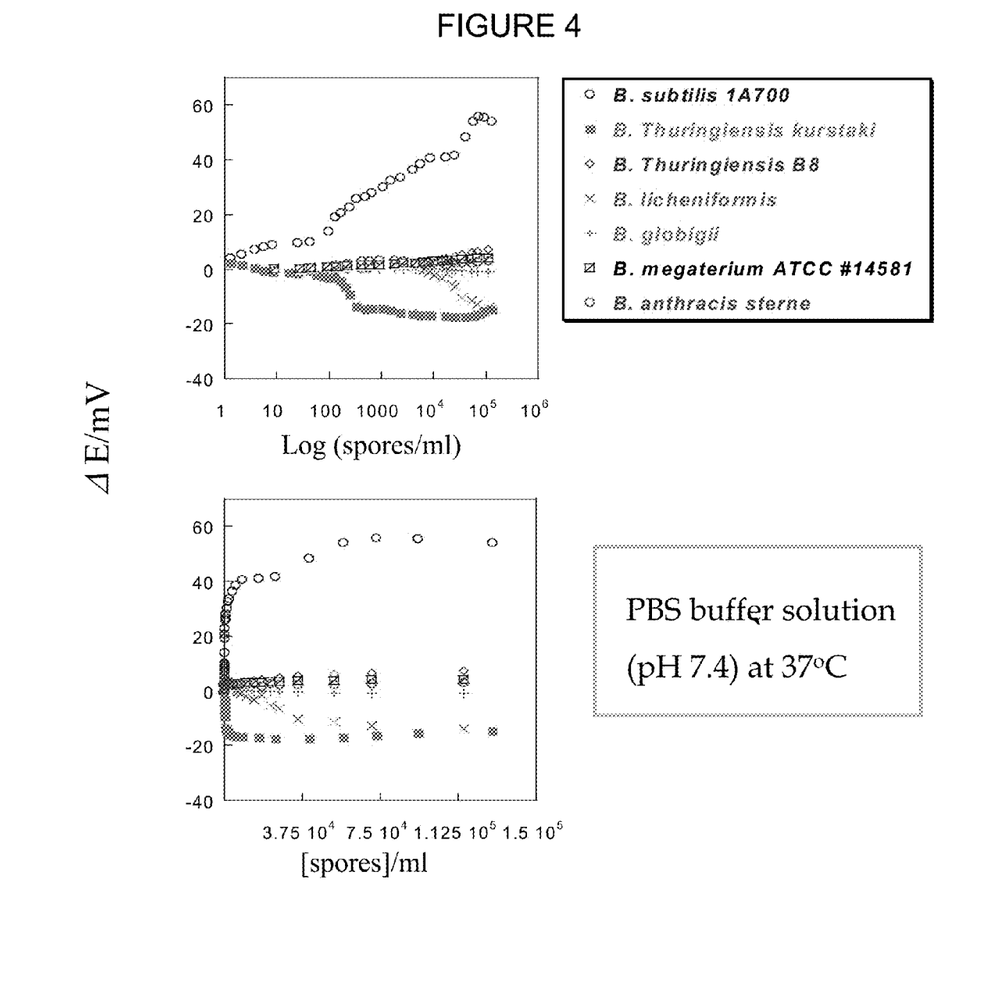
FIG. 4 is a graph (shown as both log concentration and concentration) showing the potentiometric responses of other kinds of spores on peptide/ODS sensors.
Figure 5:
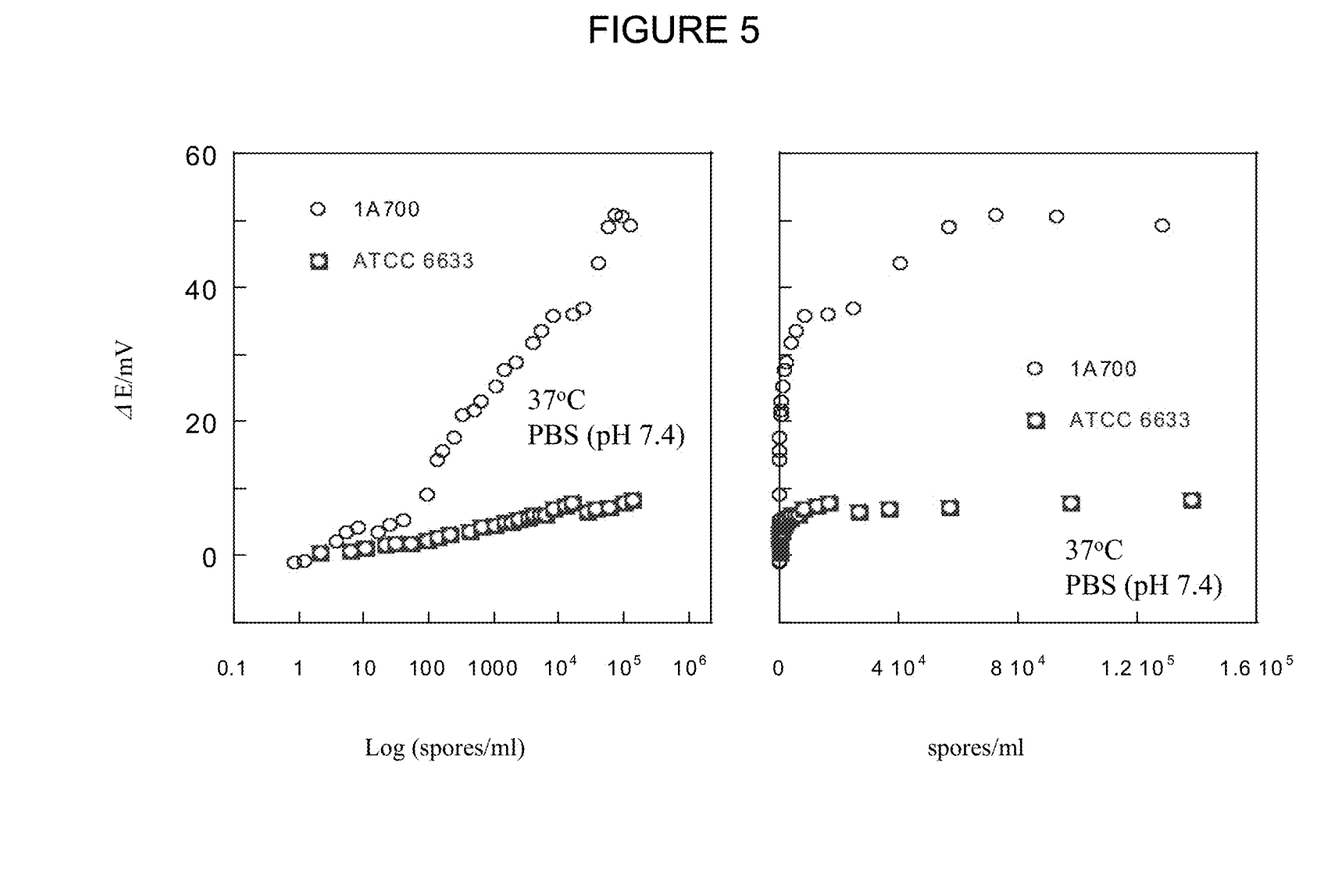
FIG. 5 is a graph (shown as both log concentration and concentration) showing the potentiometric responses of peptide/ODS sensors of *B. subtilis* strain 1A700 and *B. subtilis* ATCC 6633, respectively.

As described before and now stated alternatively, PMI is a novel method to immobilize chemical or biological molecular recognition elements (probe or ligand) on substrates. Basically, ligand (in this example, peptide) and the silylating agent (ODS) were co-adsorbed on the polar solid surface of the ITO glass plates, the ligand was incorporated into a polysiloxane monolayer by forming a hydrophobic layer of polymerized organosiloxane groups around the molecule recognition elements as depicted in FIG. 1.

The chemical or biological recognition ligand was dissolved or suspended in a low polarity medium during immobilization. The ligand could not be removed with water since the hydrophobic polymer monolayer prevents water from approaching the ligands, even though most of the ligands are water soluble. This may be due to the hydrophobic layer preventing water approach to peptide, which was surrounded by aliphatic chain. Therefore, the resulting immobilized ligand may then be used to interact with specific chemical or biological targets within a mixture of molecules, thereby enabling specific analyte to be detected and/or quantified.

Figure 7:
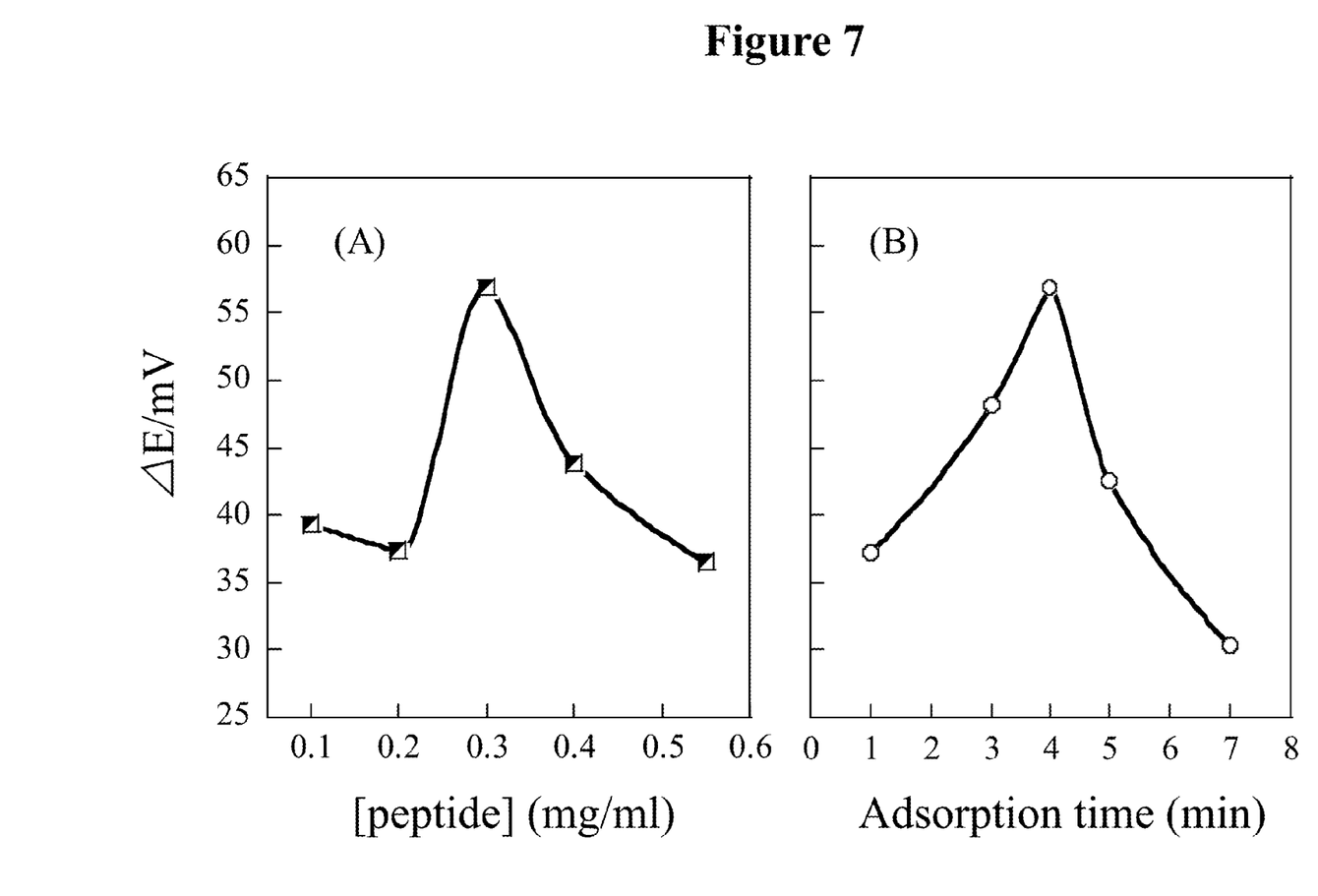

To find the optimal biorecognition conditions, the influences of the peptide concentration in the deposition solution and co-adsorption time during the fabrication of the sensors were examined. When the concentrations of peptide concentration ranging from 0.1 to 0.55 mg/ml in $CHCl_3/CCl_4$-ODS solution, the potentiometric output of those sensors is shown in FIG. 7(A).

When the concentrations of peptide is 0.30 mg/ml, the resulted sensor produced the highest potential responses to $1.3 \times 10^{-5}$ CFU/ml *B. subtilis* spores in $1.0 \times 10^{-2}$ M phosphate buffer-$1.5 \times 10^{-1}$ M NaCl (PBS buffer, pH 7.4). After the immersion of the pretreated ITO-coated plates into the solution containing ODS and peptide for time periods varying from 1 to 7 minutes, the potential responses of these electrodes were observed at *B. subtilis* spores concentrations ranging from 0.08 to $2.0 \times 10^5$ CFU/ml *B. subtilis* spores. The peak response was observed at an immersion time of approximately 4 minutes, as shown in FIG. 7(B).

The influence of incubation temperature was also investigated since it cannot be guaranteed that 37° C. will be the temperature when the sensor is used in field. At 28.5° C., the signal remains 97.7% of that produced at 37° C., and 48.6% of that produced at 23° C. Incubation temperature has a marked influence on biorecognition process and those devices can still be used at around 25° C.

Figure 8:
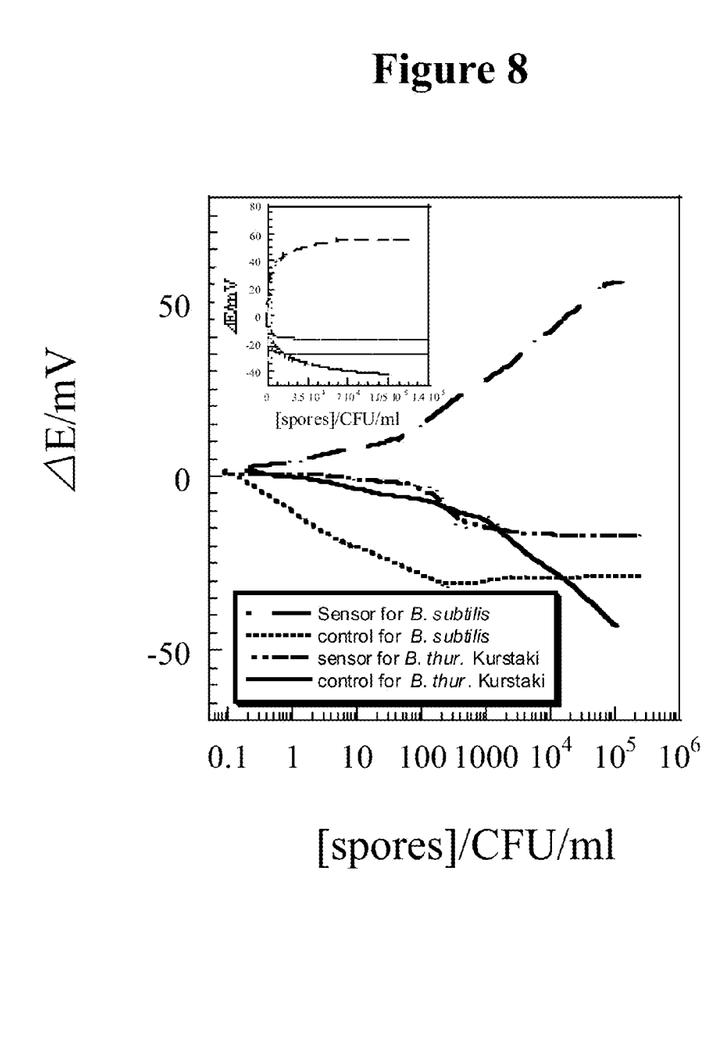

In FIG. 8, curve (----) is control (without peptide) towards *B. subtilis*. As the concentration of *B. subtilis* increases, potential output decreases. When the concentration of *B. subtilis* is 500 CFU/ml, the potential found with the control does not decrease further, and stabilizes. This characteristic indicates that *B. subtilis* has strong negative charge. However, when the peptide is immobilized in the selective layer of the sensor, the results (FIG. 8, curve (——)) demonstrated potential change in a direction opposite to that without peptide (FIG. 8, curve (----)). The potential response of the sensor to the *B. subtilis* spores in a PBS suspension was linear in the concentration range of $0.08$-$7.3 \times 10^4$ CFU/ml and the limit of detection (LOD) was 0.08 CFU/ml.

The distinctive difference in the potential outputs can be observed before and after immobilizing the peptide onto the active surface of ITO. This phenomenon indicates that peptide was successfully linked to the ITO surface. Peptide ligand (7 amino acids long) containing the consensus sequence NHFLP binds tightly, and species specifically, to spores of *B. subtilis* and forms a complex. This peptide—*B. subtilis* complex carries positive charge, which is totally different from the spores themselves (FIG. 8, curve (----)).

*B. thur.* Kurstaki spores were used to evaluate the binding of other kind of spores to the peptide/ODS surface. Curve (——) and curve (- - —— —) in FIG. 8 were potential response of a control (without peptide) sensor and a peptide sensor (with peptide) to *B. thur.* Kurstaki spores, respectively. Results obtained show that negative charge of *B. thur.* Kurstaki spores did not change after they encountered peptide. In other words, the peptide did not have any significant affinity for *B. thur.* Kurstaki spores.

In the case of *B. subtilis*, the peptide ligand appears to mimic the binding of the SpsC protein. This protein apparently binds to the surface of the forespore and may be required for the synthesis of surface polysaccharides late in the spore development. Polysaccharide deposition apparently causes *B. subtilis* spores to be hydrophilic. Genetic inactivation of the operon encoding SpsC causes *B. subtilis* spores to become hydrophobic much like spores of *B. anthracis*. Accordingly, *B. subtilis* Asps spores may provide an improved simultant for spores of *B. anthracis*.

Figure 6:
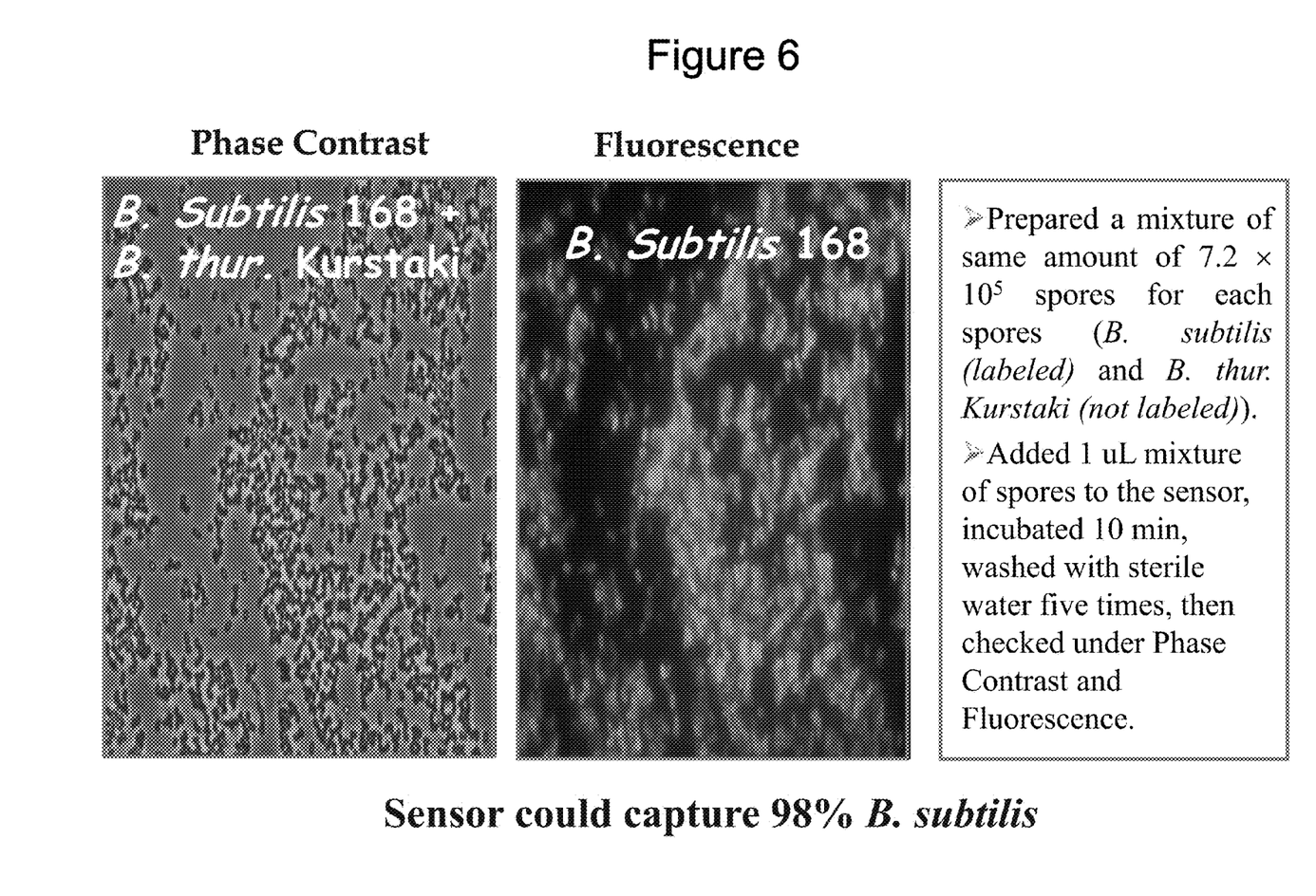
FIG. 6 includes a phase contrast microscopic image and fluorescence microscopic image of labeled spores.

Optical microscopy was also used to evaluate the binding of bacterial spores to the surface-confined peptides. A representative image of peptide sensor after reaction with $1.44 \times 10^6$ mixture of same amount of *B. subtilis* and *B. thur.* Kurstaki spores on the surface is shown in FIG. 6. Both spores were observed under phase contrast. However, only *B. subtilis* spores could be seen under fluorescence as they are labeled with fluorescence reagent, Alexa 488. Images obtained at several different locations on the surface show that the selectivity of the immobilized peptide to *B. subtilis* is 98%, due to the very similar pictures of the same sensor under phase contrast and fluorescence microscope.

Figure 9A:
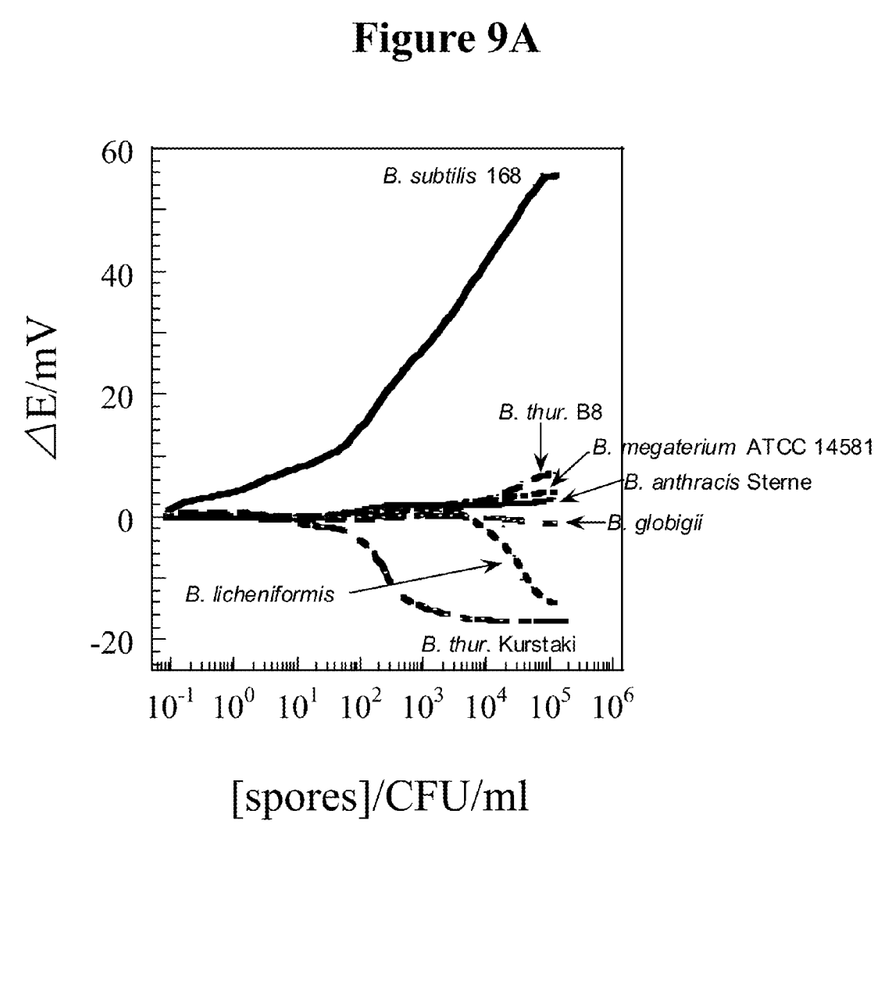

As can be appreciated, effective testing of bacteria requires methods of analysis that meet a number of challenging criteria. Selectivity and time of analysis are important characteristics related to the usefulness of microbiological testing. The biosensor system should have the specificity to distinguish the target bacteria or bacterial spores from others. FIG. 9(A) shows the potentiometric output in pH 7.4 PBS buffer upon treatment of sensing interface with same amount ($2.5 \times 10^5$ CFU/ml) but different kinds of bacterial spores. The data of potentiometric measurement in the inset figure in FIG. 9 (A) can be simulated with Nicolsky-Eisenman Equation:

$$E = E_{B.subtilis}^{0} + s\log([B.\ subtilis] + K_{B.subtilis,j}^{POT}[a_j^{z_j}]) \quad (1)$$

where $E_{B.subtilis}$ and $E_{B.subtilis}^{0}$ are the potential of the sensor and the standard electrode potential, respectively, s is the slope. $K_{B.subtilis,j}^{POT}$ (j, interference of charge $z_j$) was obtained for peptide biosensor based on simulation results of the experimental data shown in FIG. 9(A), and shown in Table 1.

TABLE 1

Potentiometric selectivity coefficients

| Spores | B. thur. Kurstaki | B. licheniformis | B. thur. B8 | B. globigii | B. megaterium ATCC 14581 | B. anthracis Sterne |
|---|---|---|---|---|---|---|
| $K_{B.\ subtilis, j}^{POT}$ | 0 | 0 | $1.0 \times 10^{-5}$ | 0 | $2.5 \times 10^{-6}$ | $12.5 \times 10^{-9}$ |

Besides *B. subtilis*, none of those bacterial spores produced any false positive potentiometric response, implying that the peptide is specific for *B. subtilis*.

Figure 9B:
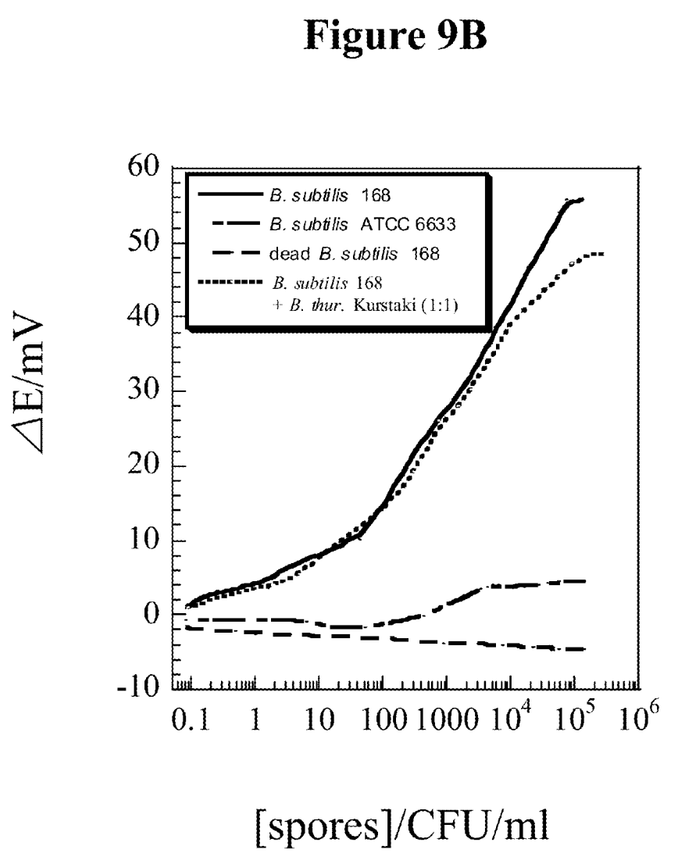

The high selectivity of our inventive biosensor also reflects in the identification of *B. subtilis* in the presence of other bacterial spores, e.g., *B. thur.* Kurstaki spores (FIG. 9(B) (blank line)). The results indicate that the sensor has almost the same potential response in the presence of the equal amounts of the *B. thur.* Kurstaki at concentration ranges from 0.08 to 9000 CFU/ml. No substantial potential difference was observed with and without *B. thur.* Kurstaki, which demonstrates a high degree of selectivity. The biosensor could distinguish *B. subtilis* from other strains of the same species, such as *B. subtilis* ATCC 6633 (FIG. 9(B)(— —)), which strain is different from *B. subtilis* 1A700. In the presence of $1.3 \times 10^5$ CFU/ml, the biosensor gives 55.8 mV to *B. subtilis* 1A700 and only 4.6 mV for *B. subtilis* ATCC 6633 demonstrating highly selective of the peptide/ODS sensor. Advantageously, even live and dead spores can be distinguished from one another. As demonstrated in FIG. 9(B),(— —), as *B. subtilis* 1A700 gave no more positive potential response after autoclaved.

Following the same facile modification of patterning and assay procedures, another kind of inventive peptide/ODS biosensor was developed for the detection of *B. anthracis* Sterne spores.

As was the case with *B. subtilis*, this peptide sequence binds tightly and species specifically to spores of *B. anthracis* Sterne solution ranging in concentration from 0.8 to $2.5 \times 10^7$ CFU/ml and forms a positive potential response complex.

Figure 10:
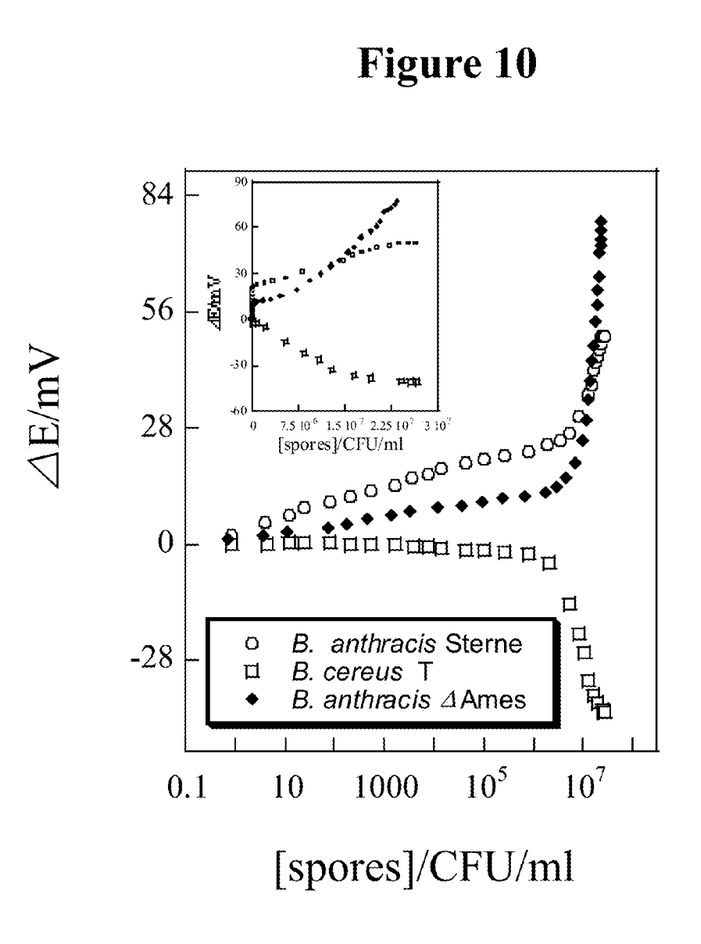

With reference now to FIG. 10, there is shown a graph depicting potentiometric responses of sensors for anthrax spores constructed according to our inventive teachings for ODI/peptide for *B. anthracis* Sterne; *B. cereus* T; and *B. antracis* Ames. As can be readily appreciated, the response is quite specific to the anthrax spores.

As can be seen by inspection of FIG. 10, *B. cereus* T (FIG. 10 (□)), which is very similar to *B. anthracis* Sterne, is undetected by our ODI/peptide sensor. And while both kinds of spores demonstrated binding by FACS analysis, potentiometric measurement advantageously provides the bias for the discrimination between *B. anthracis* Sterne and *B. cereus* T.

Additionally, the same sensor was employed to identify *B. anthracis* ΔAmes, which should have more affinity for this peptide than *B. anthracis* Sterne, as shown in FIG. 10 (♦)). As is shown in FIG. 10, when the concentration of bacterial spores $<10^7$ CFU/ml, *B. anthracis* Sterne produced a highly potentiometric output than *B. anthracis* ΔAmes, but when $>10^7$ CFU/ml, the sensor yielded higher affinity of the peptide for *B. anthracis* ΔAmes than *B. anthracis* Sterne.

Figure 11:
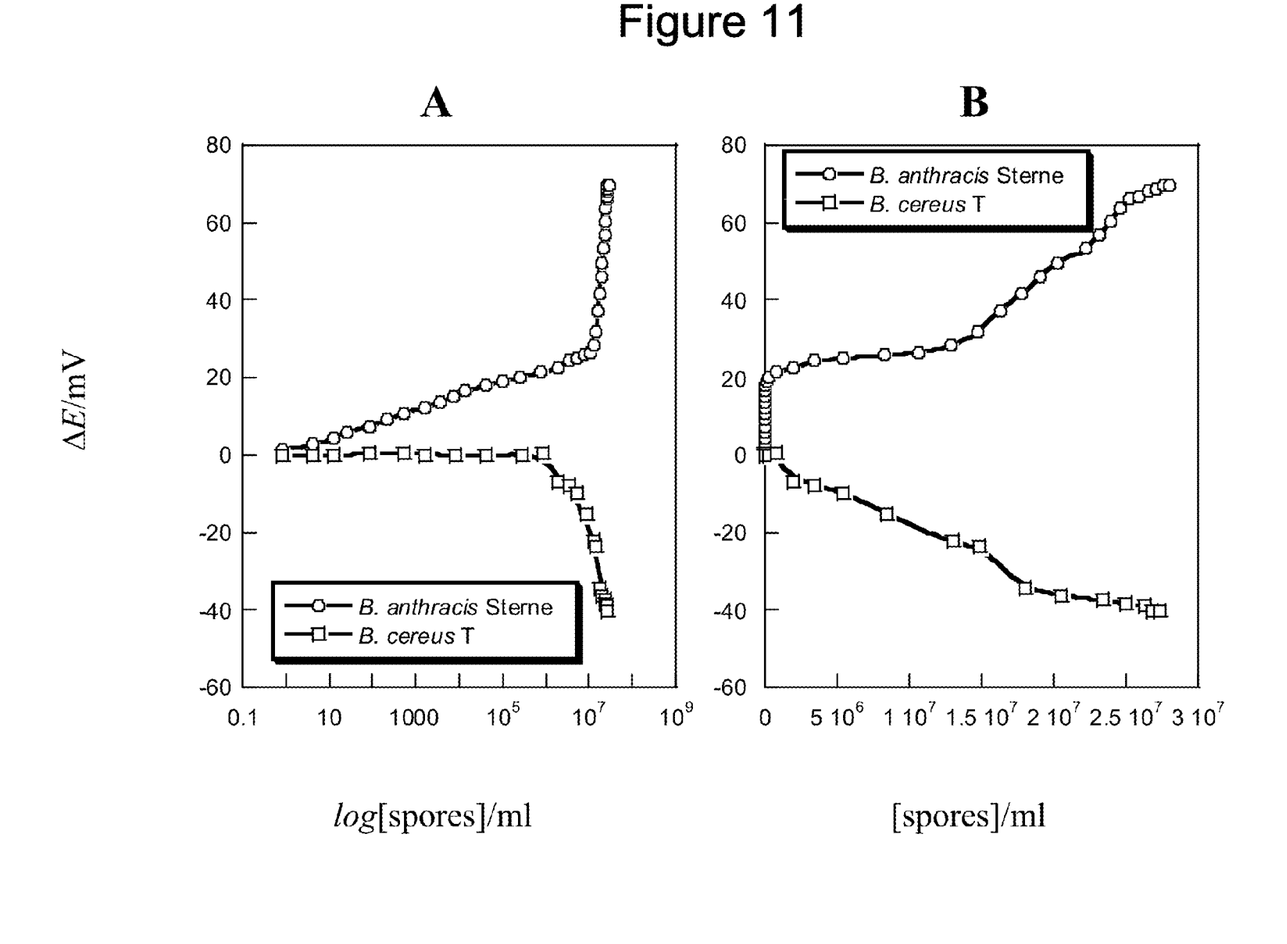

Lastly, and as mentioned earlier, there are a number of chemical or biological molecular recognition elements (probe or ligand) that may be immobilized on suitable substrates and used to provide chemical/biological specificity to a sensor. FIGS. 11(A) and 11(B) show graphs of such specific sensors.

As noted before, ligand (in this example, polylysine) and the sylylating agent (ODS) were employed. The resulting immobilized ligand (polylysine) was then be used to interact with specific chemical or biological targets, thereby enabling specific analyte to be detected and/or quantified. With reference to FIGS. 11(A) and 11(B), there is shown potentiometric measurements of *B. anthracis* Sterne and *B. cereus* T shown in both log[spores]/ml and [spores]/ml. As can be readily appreciated by those skilled in the art, our inventive methods and resulting devices are capable of providing a wide array of specific sensors and may include, for example, synthetic molecules that exhibit specific binding.

§5. Conclusions

Sensors and methods of fabricating same for the detection and identification of biological or other chemical agents, and in particular bacteria, so far are characterized by a lengthy analysis time. The assay time is usually on the order of several tens of minutes to several hours, even days. For our inventive peptide/ODS sensor, the time required to obtain equilibrium and incubation is five (5) minutes for a single test. Consequently, the biospecific reaction between, for example, *B. subtilis* spores and peptide is directly determined in real time by measuring the potentiometric changes induced by the complex formation between peptide and *B. subtilis* spores. Our inventive sensors and method of making same offers the potential to speed up the detection of anthrax and other pathogenic bacteria.

Additional problems facing the production of biosensors for direct detection of bacterial spores include the sensitivity of assay in real samples, long lifetime of the sensor and non-specific adsorption. With our inventive sensors, the limit of detection (LOD) is on the order of 8 CFU/100 ml, as described above, which is much improved compare to existed techniques.

Still further, after being stored at $-20°$ C. in a freezer for several months, the response still remained to 40% of its initial magnitude, demonstrating the long lifetime of our inventive sensors.

Various modifications to the disclosed embodiments and methods will be apparent to those skilled in the art, and the general principles set forth may be applied to other embodiments, methods and applications. Thus, the present invention is not intended to be limited to the embodiments and methods. For example, although various embodiments of the invention were described in the context of sensing biological material, the teachings of the present invention can be applied to sensing other substances, such as chemicals. Additionally, our inventive teachings should be read to include a broad array of immobilization techniques, in which a bio-active material is brought together with sufficient monomer, such that when the monomer polymerizes on a suitable substrate, the bio-active material becomes sufficiently immobilized within the polymer to create a bio-active layer(s) on the surface of the substrate. When the substrate is a suitable sensor, the sensor becomes a bio-active sensor exhibiting the specificity of the bio-active material.

What is claimed is:

1. A method for determining whether or not a solution includes specific bacterial molecules, the method comprising:
   a) providing a reference electrode in the solution;
   b) providing a working electrode in the solution, the working electrode including an electrode substrate having a layer of polymer applied thereto, and bacterial specific selector molecules,
   wherein the working electrode is constructed by exposing the electrode substrate to a suitable monomer in the presence of the bacterial specific selector molecules such that when the monomer is polymerized, the selector molecules are substantially immobilized thereto, and
   wherein the working electrode is constructed in accordance with an optimal concentration of the bacterial specific selector molecules and an optimal immersion time that are predetermined to produce a peak potential response during a testing, the optimal concentration being approximately 0.3 mg/ml and the optimal immersion time being approximately 4 minutes, and
   wherein the layer of polymer is a monolayer of Polysiloxane, and
   wherein if the selector molecules are exposed to the specific bacterial molecules, a change in electrical potential is caused;
   c) determining a potential difference between the reference electrode and the working electrode; and
   d) determining whether or not the solution includes the specific bacterial molecules using the determined potential difference.

2. The method of claim 1 wherein the bacterial specific selector molecules are peptides.

3. The method of claim 2 wherein the electrode substrate includes Indium-Tin-Oxide (ITO) glass.

4. The method of claim 3 wherein the ITO glass is treated with Sodium Hydroxide (NaOH).

5. The method of claim 1 wherein the bacterial specific selector molecules are selected from the group consisting of: peptides, proteins, enzymes, antibodies, lectin, nucleic acids, and bacterial tissue.

6. The method of claim 1 wherein the bacterial specific selector molecules are hydrophilic.

7. The method of claim 1 wherein the bacterial specific selector molecules are hydrophobic.

8. The method of claim 1 wherein the bacterial specific selector molecules are peptides specific to intact spores of *Bacillus Subtilis*.

9. The method of claim 1 wherein the bacterial specific selector molecules are peptides specific to intact spores of *Bacillus anthracis*.

10. The method of claim 1 wherein the bacterial specific selector molecules are peptides specific to intact spores of *Bacillus anthracis* Sterne.

11. The method of claim 1 wherein the reference electrode and the working electrode are provided on a solid-state electrode device.

12. The method of claim 1 wherein the bacterial specific selector molecules are synthetic molecules that exhibit selective binding to specific bacterium.

13. The method of claim 1 wherein the bacterial specific selector molecules include polylysine.

14. The method of claim 1 wherein the bacterial specific selector molecules are held to the layer of polymer by hydrophobic silanol groups.

15. The method of claim 1 wherein a potential difference between the reference electrode and the working electrode can be determined for a solution a concentration of the specific bacterial molecules of 8 CFU /100 ml.

16. The method of claim 8 wherein the potential difference between the reference electrode and the working electrode is linear for *Bacillus Subtilis* in a concentration range of 0.08-7.3×$10^4$ CFU/ml.

17. The method of claim 1 wherein the bacterial specific selector molecules are hepta peptide ligand selector molecules.

18. The method of claim 1 wherein the acts of (1) determining a potential difference between the reference electrode and the working electrode and (2) determining whether or not the solution includes the specific bacterial molecules using the determined potential difference are done in real time.

* * * * *